United States Patent [19]
Sterphone et al.

[11] Patent Number: 5,904,918
[45] Date of Patent: May 18, 1999

[54] COSMETIC POWDER COMPOSITION

[75] Inventors: Stacy M. Sterphone, Somerville; Elisa L. Burdzy, Milford, both of N.J.

[73] Assignee: L'Oreal S.A., Paris, France

[21] Appl. No.: 08/743,557

[22] Filed: Nov. 4, 1996

[51] Int. Cl.$^6$ ................................................. A61K 7/035
[52] U.S. Cl. ........................ 424/69; 424/401; 424/490; 514/844; 514/951
[58] Field of Search ............................ 424/69, 401, 490; 514/844, 951

[56] References Cited

U.S. PATENT DOCUMENTS

| | | |
|---|---|---|
| 4,159,318 | 6/1979 | Mausner et al. . |
| 4,305,929 | 12/1981 | Kawano et al. . |
| 4,305,931 | 12/1981 | Kawano et al. . |
| 4,514,383 | 4/1985 | Murray et al. . |
| 4,804,532 | 2/1989 | Busch, Jr. . |
| 4,822,600 | 4/1989 | Wortzman . |
| 4,879,175 | 11/1989 | Ugro, Jr. . |
| 5,011,690 | 4/1991 | Garvey et al. . |
| 5,030,446 | 7/1991 | Russ et al. . |
| 5,053,221 | 10/1991 | Robertson et al. . |
| 5,082,660 | 1/1992 | Ounanian et al. . |
| 5,089,269 | 2/1992 | Noda et al. . |
| 5,093,511 | 3/1992 | Yoshida et al. . |
| 5,094,852 | 3/1992 | Ohno et al. . |
| 5,112,612 | 5/1992 | Garvey et al. . |
| 5,122,418 | 6/1992 | Nakane et al. . |
| 5,135,740 | 8/1992 | Katz et al. . |
| 5,145,675 | 9/1992 | Won . |
| 5,165,915 | 11/1992 | Tokubo et al. . |
| 5,215,749 | 6/1993 | Nicoll et al. . |
| 5,234,682 | 8/1993 | Macchio et al. . |
| 5,279,830 | 1/1994 | Edmundson et al. . |
| 5,283,062 | 2/1994 | Elliott et al. . |
| 5,288,481 | 2/1994 | Ounanian et al. . |
| 5,314,683 | 5/1994 | Schlossman . |
| 5,320,834 | 6/1994 | Ounanian et al. . |
| 5,340,569 | 8/1994 | Elliott et al. . |
| 5,356,617 | 10/1994 | Schlossman . |
| 5,358,719 | 10/1994 | Mellul et al. . |
| 5,380,528 | 1/1995 | Alban et al. . |
| 5,407,746 | 4/1995 | Prengel et al. . |
| 5,411,802 | 5/1995 | Kumar et al. . |
| 5,455,048 | 10/1995 | Lahmani et al. . |

*Primary Examiner*—José G. Dees
*Assistant Examiner*—Michael A. Williamson
*Attorney, Agent, or Firm*—Baker & Botts LLP

[57] ABSTRACT

A cosmetic powder composition including a silica-sunscreen aggregate has a smooth light texture and provides ultra sheer coverage as well as enhanced sun protection to the skin.

12 Claims, No Drawings

COSMETIC POWDER COMPOSITION

BACKGROUND OF THE INVENTION

This invention relates to a cosmetic powder composition including a silica-sunscreen aggregate. The cosmetic powder composition has a smooth, light texture and provides ultra sheer coverage as well as enhanced sun protection to the skin.

The damaging effects of sunlight on the skin are well known. In order to help protect the skin from these harmful effects, sunscreen agents have been incorporated into cosmetic compositions which are applied to the skin. The incorporation of sunscreen agents into powder compositions has been limited however, by the negative textural attributes imparted by sunscreen agents to these compositions. For example, the incorporation of conventional sunscreen agents typically results in agglomeration of the powder composition, as well as an unpleasant oily feel on the skin.

SUMMARY OF THE INVENTION

Accordingly, it is an object of the invention to provide a cosmetic powder composition including at least one sunscreen which has a smooth, light feel when applied to the skin.

Another object of the invention is to provide a cosmetic powder composition which has a sun protection factor (SPF) of eight or greater.

A further object of the invention is to provide a cosmetic powder composition exhibiting enhanced flow properties.

These and other objects of the invention are achieved by providing a cosmetic powder composition comprising a cosmetically-acceptable carrier and about 3 to 20% by weight of the composition of a silica-sunscreen aggregate wherein the aggregate comprises less than 65% by weight of a porous, spherical non-fumed silica and greater than 35% by weight of at least one organic sunscreens.

The invention also provides a method of preparing a substantially oil-free cosmetic composition including preparing a silica-sunscreen aggregate by admixing, based on the total weight of the aggregate, less than 65 weight percent of porous, spherical non-fumed silica and greater than 35 weight percent of at least one organic sunscreen, and thereafter admixing about 3 to 20 weight percent of the compositions of the aggregate with a cosmetically acceptable carrier.

The invention further provides a method of enhancing the sunscreen efficacy of a cosmetic powder composition comprising the steps of providing a porous spherical non-fumed silica, admixing the spherical silica with a sunscreen to form a silica-sunscreen aggregate wherein the aggregate comprises less than 65% by weight spherical silica and greater than 35% by weight sunscreen, and admixing about 3 to 20 weight percent, based on the total weight percent of the composition, of the aggregate with a cosmetically acceptable carrier.

DETAILED DESCRIPTION OF PREFERRED EMBODIMENTS

The present invention provides a loose or pressed powder composition including a silica-sunscreen aggregate. The silica-sunscreen aggregate is present in the composition in an amount of about 3 to 20 weight percent, preferably about 3 to 15 weight percent, most preferably about 5 to 10 weight percent of the powder composition. This silica-sunscreen aggregate or silica entrapment system allows for the preparation of a substantially oil-free powder with enhanced SPF efficacy. The enhanced SPF is achieved by delivering effective amounts of sunscreen in the powder via a silica-sunscreen aggregate wherein high amounts of sunscreen are entrapped inside the silica particles. The silica-sunscreen aggregate is effective in protecting human skin from the harmful effects of ultraviolet radiation, such as sunburn and sun-induced premature aging of the skin.

Silica suitable for use in the invention includes a porous, spherical non-fumed silica. Preferably, the silica is ultrafine and has a particle size in the range of 0.5 to 20 $\mu$m, more preferably 1 to 15 $\mu$m, most preferably 1 to 5 $\mu$m. In addition, the silica should be highly porous and have a pore volume of 1 to 10 ml/g, preferably 1 to 5 ml/g. Typically, the silica has a surface area of about 300 to 1000 $m^2$/g, preferably 600 to 800 $m^2$/g. Further, suitable silicas for use in the invention should have an absorptive activity of 200 to 350 g, preferably 270 to 330 g of oil to 100 g of silica. A preferred silica for use in the powder compositions according to the invention is MSS 500/3H, a highly porous ultrafine silica available from Kobo Products, Inc., South Plainfield, N.J.

Organic sunscreens for use in the invention include any organic sunscreen which absorbs, blocks or otherwise mitigates ultraviolet radiation. Without wishing to limit the invention in any way, such sunscreen compositions include, but are not limited to, p-aminobenzoic acid, 2-ethoxyethyl-p-methoxy cinnamate, diethanolamine-p-methoxy cinnamate, digalloyl trioleate, 2,2-dihyroxy-4-methoxybenzophenone, ethyl-4-bis-(hydroxypropyl) aminobenzoate, 2-ethylhexyl-2-cyano-3,3-diphenyl acrylate, ethylhexyl-p-methoxy cinnamate, 2-ethylhexyl salicylate, glyceryl aminobenzoate, 3,3,5-trimethylcyclohexyl salicylate, lawsone with dihydroxyacetone, methyl anthranilate, 2-hydroxy-4-methoxy benzophenone, amyl-p-dimethylamino benzoate, 2-ethylhexyl-p-dimethylamino benzoate, 2-phenylbenzimidazole-5-sulphonic acid, red petroleum, 2-hydroxy-4-methoxybenzophenone-5-sulphonic acid, triethanolamine salicylate, and the like. In addition, suitable sunscreens for use in the sunscreen composition are set forth in Sunscreens Monogram, Federal Register, Vol. 58, No. 90, Proposed Rules, p. 28295 (May 12, 1993) Part B. A preferred sunscreen for use in the invention is Parsol MCX an octyl methoxycinnamate (OMC) available from Givaudan Roure.

The sunscreen is entrapped in the spherical silica by adding an organic sunscreen in liquid form or in a liquid vehicle drop-wise to a silica powder as described hereinabove to form a silica-sunscreen aggregate. The resulting mixture is a dry, non-agglomerated, sheer powder impregnated with high levels of sunscreen.

The silica-sunscreen aggregate comprises less than 65 weight percent porous, spherical non-fumed silica and greater than 35 weight percent of the at least one sunscreen. Preferably, the silica-sunscreen aggregate includes less than 50 weight percent silica and greater than 50 weight percent sunscreen, more preferably, less than 20 weight percent silica and greater than 80 weight percent sunscreen, most preferably, less than 30 weight percent silica and greater than 70 weight percent sunscreen.

The silica-sunscreen powder aggregate may be added to a substantially oil-free cosmetically acceptable carrier to provide a cosmetic powder composition having an enhanced SPF efficacy with desirable textural attributes. Such desirable attributes include an ultra-sheer, substantially oil-free powder.

Other conventional additives typically employed in cosmetic powder compositions may be employed in conjunction with the present invention. Such additives include, but are not limited to one or more preservatives such as methyl paraben, butyl paraben, propyl paraben, phenoxyethanol, benzoic acid, imidazolidinyl urea and other conventional preservatives, antioxidants, emollients, plasticizers, surfactants water proofing additives, botanical extracts and fillers including polyethylene, magnesium carbonate, methylcellulose, mica and the like.

The components of the powder compositions according to the invention are dry blended together using conventional powder blending apparatus and procedures.

The following examples illustrate preferred embodiments of a cosmetic powder composition according to the invention. It will be understood that the following examples are illustrative and not meant to limit the invention in any way.

Cosmetic Powder Formulations

| Ingredient | Formulas | | | |
|---|---|---|---|---|
| | A Wt % | B Wt % | C Wt % | D Wt % |
| Mica | 56.48 | 55.94 | 56.48 | 50.18 |
| Isopropyl Titanium Triisostearate and Boron Nitride and Acrylate Copolymer | 0.30 | 0.30 | 0.30 | 0.30 |
| Methylparaben | 0.20 | 0.20 | 0.20 | 0.20 |
| Imidazolidinyl Urea | 0.20 | 0.20 | 0.20 | 0.20 |
| Propylparaben | 0.10 | 0.10 | 0.10 | 0.10 |
| Titanium Dioxide and Aluminum Hydroxide and Stearic Acid | 3.00 | 3.00 | 3.00 | 3.00 |
| Polymethylsilsesquioxane | 2.00 | 2.00 | 2.00 | 2.00 |
| Lithium Stearate | 3.00 | 3.00 | 3.00 | 3.00 |
| Mica and perfluoropolymethylisopropylether | 5.00 | 5.00 | 5.00 | 5.00 |
| Oat Protein | 3.00 | 3.00 | 3.00 | 3.00 |
| Lauroyl Lysine | 5.00 | 5.00 | 5.00 | 5.00 |
| Octyl Methoxycinnamate and MSS 500 3/H | 6.10 | 6.10 | 6.10 | — |
| BPD-500 | — | — | 10.00 | — |
| Mica | 10.00 | 10.00 | — | 10.00 |
| M305/Aerosil R972/Parsol MCX | — | — | — | 12.40 |
| Red Oxide | 0.18 | 0.34 | 0.18 | 0.18 |
| Yellow Oxide | 0.30 | 0.56 | 0.30 | 0.30 |
| Black Oxide | 0.14 | 0.26 | 0.14 | 0.14 |
| Binder Phase | 5.00 | 5.00 | 5.00 | 5.00 |

The above powder compositions A, B, C and D were prepared as follows:

A silica-sunscreen aggregate including 26.5% spherical silica and 73.5% sunscreen was prepared by slowly adding one dropper full of Parsol MCX at a time to the spherical silica while hand mixing with a spatula until all the Parsol MCX was added. This resulted in a dry, easy flowing, non-agglomerated powder.

For comparison purposes, 36.37% Parsol MCX was added to a mixture of a polymethacrylate, M305, available from Matsumoto and fumed silica aerosil R972, available from Degussa.

All of the ingredients, except for the binder were added to a Hobart Kitchenaid mixer bowl. The ingredients were mixed for ten minutes with a wire whisk at speed number 2. The Hobart Kitchenaid mixer was powered by a variac set at 40. After ten minutes of mixing, any ingredients adhering to the sides of the mixer bowl were incorporated back into the bulk mixture. The mixture was then mixed for additional ten minutes. The resulting mixture was then passed twice through a Bantam micropulverizer equipped with a 0.013 inch herringbone screen. After collection, the pulverized material was weighed and binder was added to the collected pulverized material, taking into account any loss of material in the micropulverizer. The binder ingredient was then added to the collected pulverized material while mixing in the Hobart Kitchenaid mixer. The resulting mixture was mixed for ten minutes. After ten minutes, material adhering to the sides of the mixing bowl was reincorporated into the bulk mixture. After mixing for an additional ten minutes, the resulting mixture was passed twice through a Bantam micropulverizer equipped with a 0.027 inch herringbone screen. The collected material was then pressed into a godet using a Kemwall hydraulic hand press.

Formula A was pressed at 1200 p.s.i., Formula B was pressed at 800 p.s.i., Formula C was pressed at 3500 p.s.i and Formula D was pressed at 1200 p.s.i.

The binder included 40% neopentyl glycol dioctanoate/diisostearate and 60% octyl methoxycinnamate. The ingredient listed as a mixture of isopropyl titanium triisostearate and boron nitride and acrylate copolymer was prepared in accordance with U.S. Pat. No. 5,246,780. BPD-500 is a silica-polyurethane blend available from Kobo Products, New Jersey.

Formulas A and B were analyzed for in-vivo SPF values in accordance with the procedure set forth in "Proposed Monograph for OTC Drug Products" issued by the Food and Drug Administration, Aug. 25, 1978, Federal Register Volume 43, Number 166, 38206–38269 Each of these formulas had an SPF of 15.

The texture of Formulas A and B were superior to that of Formulas C and D. Formula C was slightly less smooth in texture than Formulas A and B, and slightly spongy when pressed at 3500 p.s.i. Comparative Formula D was rough in texture and did not feel as smooth as Formulas A and B. In addition to being substantial oil-free, these powder compositions are also substantially talc-free.

Compositions including a talc component were prepared as follows:

Cosmetic Powder Compositions

| Ingredient | E Wt % | F Wt % |
|---|---|---|
| Ultrafine Surface Modified Talc | 53.08 | 53.08 |
| Isopropyl Titanium Triisostearate and Boron Nitride and Acrylate Copolymer | 0.30 | 0.30 |
| Methylparaben | 0.20 | 0.20 |
| Imidazolidinyl Urea | 0.20 | 0.20 |
| Propylparaben | 0.10 | 0.10 |
| Titanium Dioxide and Aluminum Hydroxide and Stearic Acid | 4.00 | 4.00 |
| Polymethylsilsesquioxane | 2.00 | 2.00 |
| Lithium Stearate | 3.00 | 3.00 |
| Oat Protein | 3.00 | 3.00 |
| Mica | 20.00 | 20.00 |
| Octyl Methoxy Cinnamate and MSS 500 3/H | 6.10 | 6.10 |
| Polytrap Q5-6603 | 0.50 | 0.50 |
| Ultrafine Zinc Oxide | 1.00 | — |
| Ethylene Acrylate Copolymer Surface Treated With $TiO_2$ | — | 1.00 |
| Red Oxide | 0.28 | 0.28 |
| Yellow Oxide | 0.52 | 0.52 |
| Black Oxide | 0.22 | 0.22 |
| Binder | 5.00 | 5.00 |
| Vitamin E Nanospheres | 0.50 | 0.50 |

The silica-sunscreen aggregate was prepared as described above. The ultrafine surface modified talc is available from Luzenac Corporation, France. The talc is modified with a triglyceride such as dynasan. Polytrap Q5-6603 is an acrylate copolymer available from Dow Corning Company. The surface treated ethylene acrylate copolymer is available from Kobo Products, New Jersey.

All of the ingredients except for the binder and Vitamin E nanospheres were added to a Hobart Kitchenaid mixer bowl. The ingredients were mixed for ten minutes with a wire whisk at speed number 2. The Hobart Kitchenaid mixer was powered by a variac set at 40. After ten minutes of mixing, any ingredients adhering to the sides of the mixer bowl were incorporated back into the bulk mixture. The mixture was then mixed for an additional ten minutes. The resulting mixture was then passed twice through a Bantam micropulverizer equipped with a 0.013 inch herringbone screen.

The binder and Vitamin E nanospheres were separately mixed together with a spatula until homogeneous. The binder was prepared adding 35 g of neopentyl glycol dioctanoate/diisostearate to 60 g of octyl methoxycinnamate. Five grams of a silicone derivative, Abil Wax 9801, available from Goldschmidt Chemical was then added to form the resulting binder.

The binder and Vitamin E mixture were added drop-wise to the other ingredients while stirring in the Hobart Kitchenaid mixer. After ten minutes of mixing any ingredients adhering to the sides of the mixer bowl were incorporated back into the bulk mixture. The mixture was then passed twice through a Bantam micropulverizer equipped with a 0.02 inch herringbone screen. The collected material was mixed again for five minutes. Any ingredients adhering to the sides of the mixer bowl were incorporated back into the bulk mixture.

Formulas E and F were pressed into a godet as described above at a pressure of 1100 p.s.i. The SPF of these formulas was analyzed as described above. Formulas E and F had an SPF of 15.15 and 13.8, respectively.

Entrapping an organic sunscreen in a spherical silica in accordance with the invention enables the cosmetic powder to support a high level of sunscreen without incorporating the negative textural attributes which usually result from the use of higher levels of sunscreens. In addition, the silica-sunscreen aggregate enhances the flow properties of the cosmetic powder composition thereby facilitating product manufacture and processing. The use of the spherical silica also enhances the smooth texture or feel of the powder composition on the skin.

Although this invention has been illustrated by reference to specific embodiments, it will be apparent to those skilled in the art that various changes and modifications may be made which clearly fall within the scope of this invention.

We claim:

1. A method of preparing a cosmetic composition comprising:
   (a) preparing a silica-sunscreen aggregate by admixing, based upon the total weight of the aggregate, less than 65 weight percent of porous, spherical non-fumed silica and greater than 35 weight percent of at least one organic sunscreen; and
   (b) admixing about 3 to 20 weight percent, based upon the total weight of the composition, of the aggregate with a cosmetically acceptable carrier.

2. A method of preparing a cosmetic composition according to claim 1 comprising preparing a silica-sunscreen aggregate by admixing, based on the total weight of the aggregate, less than 50 weight percent of porous, spherical non-fumed silica and greater than 50 weight percent of at least one organic sunscreen.

3. A method of preparing a cosmetic composition according to claim 2 comprising preparing a silica-sunscreen aggregate by admixing, based on the total weight of the aggregate, less than 30 weight percent of porous, spherical non-fumed silica and greater than 70 weight percent of at least one organic sunscreen.

4. A method of preparing a cosmetic composition according to claim comprising preparing a silica-sunscreen aggregate by admixing, based on the total weight of the aggregate, less than 20 weight percent of porous, spherical non-fumed silica and greater than 80 weight percent of at least one organic sunscreen.

5. A method according to claim 1, claim 2, claim 3 or claim 4 comprising admixing about 3 to 15 weight percent, based upon the total weight of the composition, of the aggregate with a cosmetically acceptable carrier.

6. A method according to claim 5 comprising admixing about 5 to 10 weight percent, based upon the total weight of the composition, of the aggregate with a cosmetically acceptable carrier.

7. A method of enhancing the sunscreen efficacy of a cosmetic powder composition comprising the steps of:
   providing a porous spherical non-fumed silica;
   admixing the spherical silica with a sunscreen to form a silica-sunscreen aggregate wherein the aggregate comprises less than 65% by weight spherical silica and greater than 35% by weight sunscreen; and
   admixing about 3 to 20 weight percent, based on the total weight percent of the composition, of the aggregate with a cosmetically acceptable carrier.

8. A method of enhancing the sunscreen efficacy of a cosmetic powder composition in accordance with claim 7 comprising admixing the spherical silica with a sunscreen to form a silica-sunscreen aggregate wherein the aggregate comprises less than 50% by weight spherical silica and greater than 50% by weight sunscreen.

9. A method of enhancing the sunscreen efficacy of a cosmetic powder composition in accordance with claim 8 comprising admixing the spherical silica with a sunscreen to form a silica-sunscreen aggregate wherein the aggregate comprises less than 30% by weight spherical silica and greater than 70% by weight sunscreen.

10. A method of enhancing the sunscreen efficacy of a cosmetic powder composition in accordance with claim 9 comprising admixing the spherical silica with a sunscreen to form a silica-sunscreen aggregate wherein the aggregate comprises less than 20% by weight spherical silica and greater than 80% by weight sunscreen.

11. A method of enhancing the sunscreen efficacy of a cosmetic powder composition in accordance with claim 7, claim 8, claim 9 or claim 10 comprising admixing about 3 to 15 weight percent, based on the total weight percent of the composition, of the aggregate with a cosmetically acceptable carrier.

12. A method of enhancing the sunscreen efficacy of a cosmetic powder composition in accordance with claim 11 comprising admixing about 5 to 10 weight percent, based on the total weight percent of the composition, of the aggregate with a cosmetically acceptable carrier.

* * * * *

UNITED STATES PATENT AND TRADEMARK OFFICE
CERTIFICATE OF CORRECTION

PATENT NO. : 5,904,918  
DATED : May 18, 1999  
INVENTOR(S) : Sterphone, et al.

Page 1 of 1

It is certified that error appears in the above-identified patent and that said Letters Patent is hereby corrected as shown below:

Claims column 6,
Line 4, "claim" should read -- claim 3 --

Column 1,
Line 36 "sunscreens" should read -- sunscreen --

Column 3,
Line 2 "tants water" should read -- tants, water --

Signed and Sealed this

Twenty-first Day of August, 2001

Attest:

*Nicholas P. Godici*

NICHOLAS P. GODICI
*Attesting Officer*     *Acting Director of the United States Patent and Trademark Office*